United States Patent [19]

Baker et al.

[11] Patent Number: 4,527,953
[45] Date of Patent: Jul. 9, 1985

[54] PUMP UNIT FOR SAMPLING AIR

[75] Inventors: W. Barry Baker, Newark, Del.; Harry E. Betsill, Timonium, Md.

[73] Assignee: E. I. Du Pont de Nemours and Company, Wilmington, Del.

[21] Appl. No.: 660,053

[22] Filed: Oct. 12, 1984

[51] Int. Cl.³ .................... F04B 49/00; F04B 49/06; F04B 39/16; F04B 11/00
[52] U.S. Cl. ....................... 417/38; 417/43; 417/63; 417/411; 417/540
[58] Field of Search ............... 417/38, 63, 43, 440, 417/540, 411

[56] References Cited

U.S. PATENT DOCUMENTS 4,246,788  1/1981  Olin et al. ............... 73/863.03
4,384,825  5/1983  Thomas et al. ................ 417/63

Primary Examiner—William L. Freeh
Attorney, Agent, or Firm—Hilmar L. Fricke

[57] ABSTRACT

An improved pump unit for sampling air that operates at a constant air flow rate in the range of 5–5000 cc/min. having a filter for removing particles or vapors from the air stream, an air accumulator, a variable drive pump optionally with a bypass, an electric motor for driving the pump, an optional air reservoir, an orifice which creates a pressure drop in the air stream, an optional bypass for the orifice and a pressure switch connected in parallel to the orifice which monitors a change in the air pressure drop; the improvement in the pump is the use of a digital circuit electrically connected to the pressure switch and a closed loop control means electrically connected to the digital circuit and motor; a digital signal determines the open or closed position of the switch and the control means and allows current to flow or not flow to the motor driving the air pump to provide a constant flow of air through the unit; the pump unit is worn by a worker or is placed in a work area and at the termination of a period of time, such as a work day, the filter is removed and the contents collected are analyzed by conventional techniques such as gas chromatography to determine a level of exposure of the individual or the level of exposure of people working in that area.

21 Claims, 2 Drawing Figures

4,527,953

PUMP UNIT FOR SAMPLING AIR

BACKGROUND OF THE INVENTION

This invention is related to an air sampling pump unit and in particular to an improved air sampling pump unit designed for use by an individual.

Air sampling pump units having a constant air flow rate are used to monitor air to which workers are exposed. These pump units are well known in the art. Typical examples of such pump units are shown in Baker et al. U.S. Pat. No. 4,063,824 issued Dec. 20, 1977, Baker et al. U.S. Pat. No. 4,123,932 issued Nov. 7, 1978, Wells U.S. Pat. No. 4,257,746 issued Mar. 24, 1981 and Baker U.S. Pat. No. 4,269,059 issued May 26, 1981. These pump units are excellent for the particular use for which the pump units were designed. However, there is a need for a versatile pump which can accurately pump air at very low flow rates such as 5 cc/min. to very high flow rates such as 5000 cc/min. Also, it would be desirable to have the following features on the pump unit: user programmable starting time, running time, and tolerated restricted air flow time; measure air temperature; have memory retention of program; have memory retention after the unit is turned off; have a liquid crystal display which shows values of flow, time and temperature and a computer interface which will allow loading of data into a computer and allow loading of operational data into the pump unit.

In the operation of the aforementioned prior art air sampling pump units, the pump is controlled through a pressure switch positioned in parallel to an orifice which monitors pressure drop across the orifice caused by a change in air flow. For example, if there is a blockage of air flow, the pressure switch closes and through an integrator circuit and an amplifier circuit provides an increased voltage to the motor driving the pump and thereby increases the air flow. When the pressure drop across the orifice returns to normal, the pressure switch opens and the pump operates under usual conditions. The pressure switch also constantly opens and closes with pulsations in air flow caused by pulsations of the pump. Under extremely severe operating conditions such as opening and closing of the switch several hundred times a minute, the electrodes of the pressure switch rapidly deteriorate because of electrical arcing across the electrodes. An improvement that is required would determine whether or not the switch was open or closed without applying a constant voltage across the switch to generate an electrical signal.

The improved air sampling pump unit of this invention pump units air accurately at very low and high rates, is user programmable to start and run for a period of time, measures temperatures, has a memory retention, a liquid crystal display and measures the on-off position of the pressure switch without applying a constant voltage across the switch and controls the air pump via a computer and allows for loading and unloading of data.

SUMMARY OF THE INVENTION

An improved pump unit for sampling air and having a constant air flow rate through the unit; the unit having an air intake, a filter means for removing particles or vapors from the air tubularly connected to the air intake, a variable drive air pump connected to the filter means which pump units an air stream through the unit, a variable electric speed motor connected to the pump, a power source for the motor, an orifice positioned in a tubular connection coupled to the pump and causes an air pressure drop in the air stream being pumped through the pump unit, a differential pressure switch with an open and a closed position tubularly placed in parallel relationship to the orifice and is activated by a change in air pressure drop of the airstream caused by a change in air flow through the unit, an exhaust port tubularly connected to the orifice and the differential pressure switch; the improvement that is used therewith is as follows:

digital circuit electrically connected to the pressure switch and a closed loop control means electrically connected to the digital circuit, the power source and the motor; wherein the digital circuit sends a digital low duty cycle pulse signal over a set time interval to determine the predominant open or closed position of the switch during the time interval; in the event the switch is in the predominant open position, the control means gradually increases voltage from the power source to the motor thereby driving the motor at an increasing speed which in turn drives the pump at an increasing speed and increases air flow through the unit; in the event the switch is in the predominant closed position, the control means gradually decreases voltage from the power source to the motor thereby driving the motor at a decreasing speed which in turn drives the pump at a decreasing speed and decrease air flow through the unit; whereby the air flow through the unit is maintained at a constant flow rate.

DETAILED DESCRIPTION OF THE INVENTION

The air sampling pump unit is of a compact size and is designed for individual use. The unit measures about 5.7×10.2×12.7 cm. and weights about 800–1100 gms depending on the weight of the battery pack used in the unit.

The air sampling pump unit with its constant flow feature and excellent accuracy can be used to monitor air which may contain environmental hazards to which individuals may be exposed. For example, vinyl chloride vapors can be monitored in a work place, toxic radon gas and related gas in mines can be monitored, coal dust in mines and pits can be monitored. The filter of the air sampling pump unit is analyzed for the substance being monitored at the end of a work period, such as an eight hour work day, and results are recorded in a workers file. If a worker is exposed to a hazard over a specified amount, he is reassigned to another job.

Figure 1:
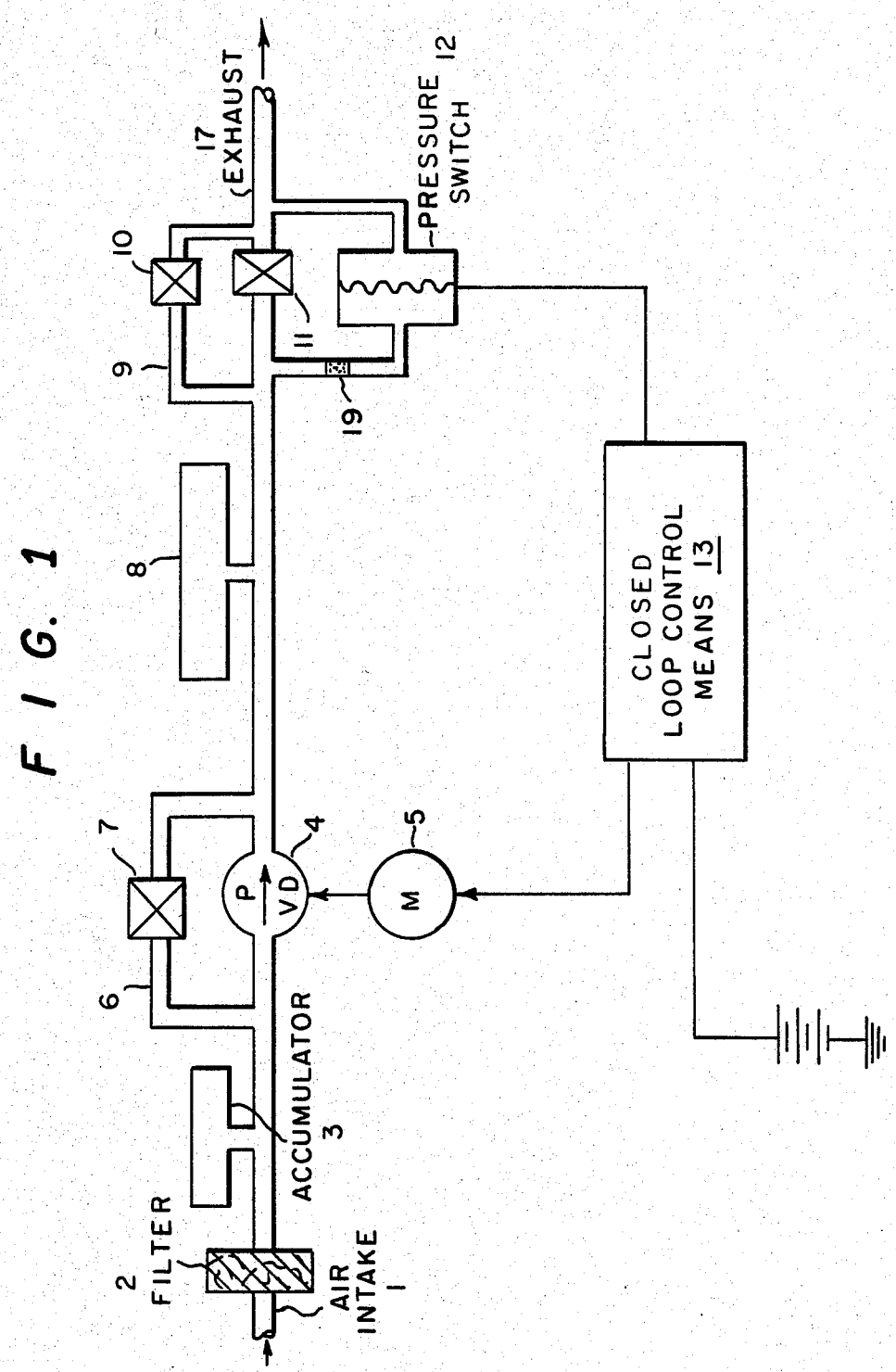
FIG. 1 shows a block diagram of the pump unit.

Referring to the block diagram of FIG. 1, air is pulled into the intake 1 and through the filter 2 and preferably into an accumulator 3 by the variable drive air pump 4 driven by a variable speed motor 5. The pump can operate without a bypass and a bypass valve but for low flow rates a bypass and valve are preferred. A bypass valve 7 is positioned in parallel to the pump 4 in tube 6. The bypass valve is usually an adjustable needle valve and is adjusted to provide the desired air flow rate. By opening the valve, more air is recycled thereby reducing the air flow rate through the unit. By closing the valve, more air flows through the unit. The pump can operate smoothly at a normal speed providing low air flow rates with the bypass open rather than operating slowly and sticking and binding in the event the bypass was not used for low air flow rates.

An air reservoir need not be used but is highly preferred. The air reservoir 8 is positioned in the tube or channel connecting the pump 4 to the orifice 11. The air reservoir helps reduce pulsations caused by the pump and in general helps provide a smooth flow of air through the unit.

An orifice 11, usually an adjustable needle valve or a fixed orifice, is positioned between the air reservoir 8 and the exhaust 17. The orifice causes an air pressure drop which is monitored by pressure switch 12 which opens and closes with a change in the pressure drop. Preferably, in parallel with the orifice is a bypass which comprises a tube or a channel 9 in which a valve 10 such as an adjustable needle valve is positioned. Valves 10 and 11 are similar in function. Valve 11, the orifice, functions as a course control and valve 10, the by-pass valve, functions as a fine control.

In channel or tube 18 in which the pressure switch 12 is positioned, a filter 19 usually of a rubber foam is positioned in the channel. This filter reduces and modulates pump pulsations to the pressure switch.

Changes in the air flow through the unit which can be caused by a blockage, either partial or complete, of the air intake or air filter or by pulsation caused by operation of the pump causes changes in the air pressure drop and causes the pressure switch to open and close. Electrically coupled to the pressure switch is a closed loop control means 13 which preferably is a computer and motor driven circuit.

The computer sends a digital low duty cycle pulse signal over a set time interval to the pressure switch to determine the predominant open or closed position of the switch during the time interval. In the event the switch is in the predominant open position, the control means of the computer gradually increases voltage from the power source which through the motor driver circuit drives the motor at an increase speed which in turn drives the pump at an increased speed and increases air flow through the unit. In the event the pressure switch is in a predominantly closed position, the control means gradually decreases the voltage from the power source which through the motor driver circuit decreases the speed of the motor and pump and decreases air flow through the unit.

A constant voltage is not directly applied across the electrodes of the pressure switch 12 as was done with prior art pump units. In these prior art pump units excessive opening and closing of the pressure switch caused the switch to wear out very rapidly since arcing across the electrodes took place on opening and closing of the switch. In a relatively short time, the electrodes were burned and pitted. In the present invention, a voltage is not applied across the pressure switch. The digital signal from the computer determines whether or not the switch is predominantly closed or open. The signal voltage is applied for a very short time and eliminates virtually all of the arcing across the electrodes of the switch.

Preferably, an LCD (liquid crystal display) driver unit is electrically coupled to the computer and feeds a signal to a LCD (liquid crystal display) which displays data that has been accumulated by computer of the unit.

The filter 2 of the pump unit can be adapted to entrap almost any type of substance such as gases, liquids of solids. If mechanical filtration is only required, for example, to collect dust particles to which a worker is exposed, a filter is provided which will entrap particles of 0.01 microns or larger. If the filter is to entrap a gas such as sulfur dioxide, a chemical filter is used which will entrap this gas. If vapors are to be entrapped, then a filter such as a charcoal filter, is used which entraps vapors. At the end of the period which an individual is wearing the unit, such as an 8 hours work day, the filter is removed and examined for the substance or substances to which the individual was exposed. A simple count of particles under a microscope may be used or the filter can be analyzed, for example, with a gas chromatograph.

The accumulator 3 is usually an integral part of the frame of the pump unit and is milled, molded or cut into the frame with an elastomer sheet covering one wall and with appropriate openings. A typical accumulator has a volume of about 2 to 20 cc and reduces and moderates surges created by the pump and allows a build-up of air on the suction side of the pump.

A variable drive air pump is used in the dosimeter. Generally, a diaphragm type pump is used that pump units from about 5 to 5000 cubic centimeters per minute. Other pump units such as piston pump units, rotary pump units and centrifugal pump units can also be used.

The pump is electrically connected to a conventional D.C. motor of about 0.0001–0.02 horsepower. The motor is a variable speed motor and operates from about 80 to 8000 revolutions per minute. Under some circumstances, a reducing gear can be used between the motor and the pump.

The reservoir 8 is usually an integral part of any framework on which the various components used in the unit are mounted. Part of the reservoir may be enclosed with a thin sheet of an elastomer so that any pulsations of the air stream created by the pump can be readily dampened by the elastomer absorbing the pulsation.

The purpose of the reservoir is to smooth any pulsations of the air stream created by the strokes of the pump at least to some degree before the air stream passes through the orifice. The volume of the reservoir is as small as possible but of sufficient volume to reduce the pulsations of the air stream usually has a volume similar to the volume of the accumulator.

An orifice typically as an adjustable needle valve, is positioned in a tube connecting the reservoir to the exhaust port. An orifice is used that creates a pressure drop of about 0.4–4.0 inches of water. Usually a pressure drop of 2.5–3.5 inches of water is used.

A differential pressure switch of a relatively high level of sensitivity is used and is sensitive to a pressure drop change in the air stream of about 0.1–0.5 inches of water.

One useful closed loop control means comprises a digital circuit electrically connected to the pressure switch and to an integrator circuit that is connected to the power source which integrates the signal from the digital circuit and sends this integrated signal to an amplifier circuit. The amplifier circuit is connected to the power source and in series to the integrator circuit and the electric motor and feeds an amplified signal to the motor and drives the motor at the appropriate speed for uniform air flow through the pump unit.

The digital circuit provides pulses in the range of 50-1000 puluses per second to the pressure switch. The pulses have a duty cycle of 0.1-5%. This limits the range of effective current to the switch to about 0.1-5.0 milliamps.

Another closed loop control means for controlling the motor comprises the digital circuit electrically connected to the pressure switch a digital integrator circuit connected to the digital circuit. The integrator circuit receives and integrates the signal received from the digital circuit. A digital to analog converter is connected to the integrator circuit and converts the signal to an analog signal which is sent to an amplifier circuit connected to the motor and drives the motor as appropriate speed to achieve uniform air flow through the unit.

In one preferred closed loop control means, the digital circuit is connected to a digital integrator circuit which integrates the digital signal received from the pressure switch. This integrated signal is then fed to a digital pulse width modulator switching device connected to the digital integrator circuit. This switching device is connected to the power source and the motor and feeds current to the motor to operate the motor and hence, the air pump such that a uniform flow of air is passing through the unit.

Figure 2:
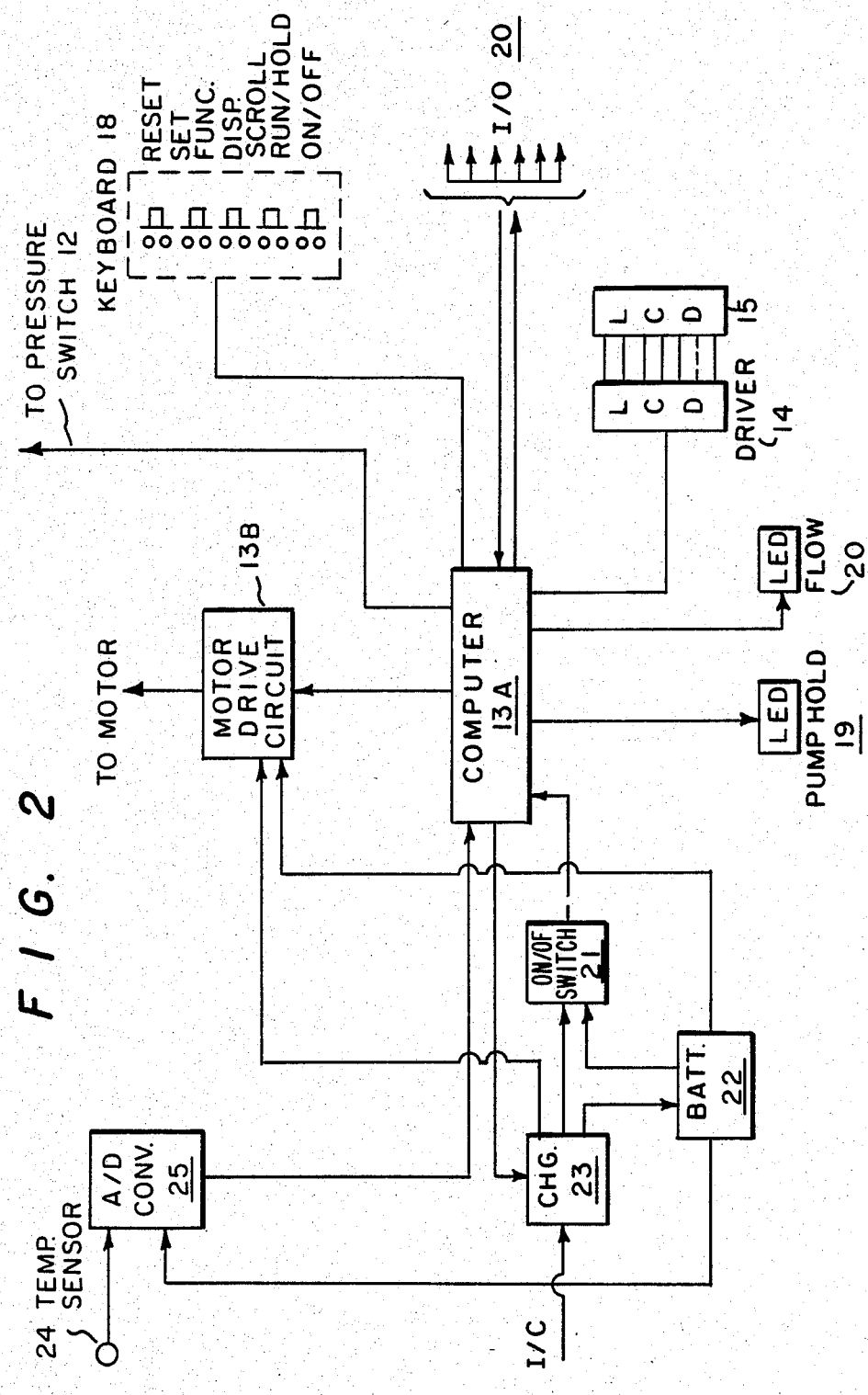
FIG. 2 shows a block diagram for the electronic circuit of the pump unit.

Referring to FIG. 2, the above preferred control means is incorporated into a computer 13A which is electrically connected to the motor drive circuit 13B which amplifies the signal from the computer and drives the motor 5. The digital circuit and digital integrator are part of the computer circuit. The digital pulse signal from the computer 13A is sent to the pressure switch. The pulse width modulator switching device is part of the motor drive circuit 13B which drives the motor. A keyboard 18 is used to enter data and select program limit parameters is connected to the computer. Electrically attached to the computer 13A is a LED (light emitting diode) which is activated when the pump is in the hold position and not operating. A second LED 20 is activated when flow through the pump is in control.

The LCD Driver 15 attached to the computer feeds a signal to the LCD 14 which displays data which has been accumulated by the computer 13A.

An I/O device 20 (Input Output device) is a device that permits a data buss to be attached to the computer and allows for unloading of data to a second computer for recording. The I/O device also allows for loading data into the computer such as operating parameters, run time, low flow time and the like. This can be accomplished with a programmer unit known in the art. This loading technique is particularly useful when a number of pump units must be programmed for the same information. For example, a shift of 50 people working in a mine or plant are each given a pump unit to wear during the shift. Programming each unit individually would be time consuming. By using the programmer, each unit can be loaded with the desired program within 10 seconds or less.

The unit is activated with an ON/OFF switch 21 electrically attached to the battery BATT 22 and the computer 13A. A battery charger circuit CHG 23 attached to the battery 22 changes the battery but also can be used to drive the motor through Motor Drive circuit 13B. I/C shown attached to the charge is an outside power source that provides power to the charger.

A temperature sensor 24 is connected to an analog/digital converter A/D 25 which in turn is connected to the computer 13A. The A/D converts the temperature signal and any other analog signals which may be received for other functions to digital signals which can be processed by the computer 13A.

The following is a more detailed description of the functioning of the components of the pump unit shown in FIG. 2.

Computer

The computer 13A typically is an 80C49 CMOS single chip microcomputer and is the central controller for the pumps unit. The microcomputer's primary function is to provide closed loop control of the pump motor based on the state of the pressure switch at the time of periodic samples. Control of the motor is via pulse width variation to the motor control circuitry. In addition to this the microcomputer performs the house keeping functions such as keeping run time, low flow time, display data presentation, local control switch monitoring and responses, battery charge timing and control, temperature monitoring, and external communication.

Since the microcomputer contains the CPU, I/O, data RAM and program memory internally a minimum of external circuitry is required to support its operation. Typically, a 6 MHz crystal, and two capacitors and establish the computer instruction cycle timing time base. One capacitor performs the power up reset function. A transistor, typically a VN 2222L, which is in parallel with a capacitor is required to allow computer controlled turn-off.

The keyboard 18 and LED indicators 19 and 20 are under direct control of the microcomputer. The operator uses the keyboard to affect local control and select program limit parameters. In the simplest mode of operation where parameters are selected locally, the pump has three states. On power-up initiated by depression of the ON/OFF key the computer comes up in the HOLD mode. In this mode it is possible to select runtime parameters including run time, low flow time, and start delay. This is done by using the DISP SCROLL to select the parameter to be changed and pressing the SET FUNC key to scroll through the available parameters. Depressing the RUN/HOLD key will then force the pump into the RUN state where the motor is under control of the computer. Once the computer has been forced into the RUN state it may be returned to the HOLD state to stop the pump motor, however it is not possible to change the programmed parameters. The last state is selected by the ON/OFF key. When this button is pressed the computer is placed in the OFF state and a 20 minute timer is started. If the pump remains in the OFF state until this timer times out the computer generates a shut-down pulse which removes power to itself. In the OFF state two successive depressions of the RESET key will force a return to the initial power-up HOLD state.

DISPLAY INTERFACE (LCD)

The pump unit states and the parameters are presented to the operator via an LCD display 15 capable of full numeric character display and limited alpha character display. The LCD display, is interfaced to the microprocessor via the LCD Driver 14 which typically is a MM5453 serial input LCD interface chip. The driver interface requires a data and clock input from the computer. These two outputs are also made available via the external interface connector.

In normal operation of the pump unit, the LCD is not visible to the user. Two LEDs are provided to give minimum operational information to the user. The HOLD LED is ON when the computer is in the HOLD or OFF state to indicate that the pump is not actively taking a sample. The FLOW LED, is used to indicate flow status. A continuous ON LED indicates that the pump is under control of the microcomputer. A flashing LED indicates that a low flow condition exists.

TURN-ON LOGIC AND POWER SUPPLY

As stated above the pump is activated by depression of the ON/OFF key of the keyboard but once the circuitry is powered-up turn-off is under the control of the microcomputer. Turn-on is also performed when the battery charger 23 is connected. The turn-on logic function is performed by discrete digital circuitry in conjunction and with micro computer.

The shut-down function is controlled by this digital circuitry and microprocessor. While the battery charger is connected the power supply, latch is forced to the on state and shut-down is precluded.

MOTOR DRIVE CIRCUITRY

The motor drive circuitry comprises discrete transistors, resistors and an operational amplifier. The motor is controlled by the microcomputer using a pulse width technique. The pulse width is variable in 0.1% steps over a range of approximately 3% to 97% duty cycle.

A current limit circuit in conjunction with the motor is key to allowing the pump to run continuously from the battery charger as well as establishing the minimum voltage to the microcomputer during the time the pump is operating. The magnitude of the maximum current was established by the normal running current of the motor, the voltage drop across the current limiting resistor in the battery, and the current required to charge the batteries. Note that the current to the motor is only peak limited. When the motor is rotating fast enough to develop a back EMF, the peak current is determined by the motor and not the current limiting circuitry. At very low flow rates the current limit circuit is functional which tends to give better motor response to the pulse width variation of the control loop.

ANALOG TO DIGITAL INTERFACE

The analog to digital interface circuitry, and A/D converter 25 on FIG. 2., is included to allow monitoring of the battery voltage and measurement of the temperature. This function is performed by a temperature sensor under control of the microprocessor. The A/D converter 25 typically is is a four channel, 8 bit, serial analog-to-digital converter. Channels 0 and 1 of U6 are used in a differential mode to measure temperature while channel 2 is used to monitor the battery voltage. Channel 3 has been implemented as a test input.

All analog-to-digital conversions are keyed to the pulse width control of the pump motor and take place at the end of the cycle when the pulse is off. This minimizes the current drain of the analog-to-digital circuits and also minimizes the self heating in the temperature sensor which can produce errors in the temperature reading.

The temperature sensor, typically is a LM335 band gap reference with an output voltage of 10 millivolts/-degree Kelvin. Temperature can thus be quantized to 0.5 degrees over a range of $-28$ to $+99.5$ degrees Celsius. When the pump is first powered up and until the pump motor is started the temperature is available to the operator as the ambient temperature. Once the program has started (motor started) the average temperature over the run is computed and available for display.

The battery voltage is also measured during the off time of the motor. Since the motor can not be on while the battery voltage is measured, a close estimate of the battery open circuit potential is available to the microcomputer. This measurement is used by the microcomputer to determine two critical voltage. At 5.5 VDC the pump circuit is automatically disabled to save the memory in the microcomputer. This state is indicated to the user by flashing decimal points in the LCD display. At 5.0 VDC the microcomputer shuts down to prevent reversal of a cell in the battery pack.

EXTERNAL DATA INTERFACE

An external data interface is provided, shown on FIG. 2 as I/O 20. The primary purpose of this interface is to allow data to be read by an external computer device and program parameters such as start time, run time, low flow time and time of day to be down loaded to pump by a higher level device. When programmed externally the pump has features not available from the front panel controls. These features are activated by turning the pump on and connecting the programmer device and down loading the desired program parameters. When programmed in this manner the pump has the capability to start at a specified time of day, a run time specified in hours and minutes, a low flow time specified in minutes and seconds, and the ability to provide intermittent grab samples. In the latter feature the pump can be programmed to run a given number of minutes out of each hour.

The external interface also provides as means of paralleling remote displays, monitoring critical voltages and powering the pump from sources other than the battery.

BATTERY CHARGING CIRCUIT

Battery charging, shown as CHG. 23 FIG. 2, is under the direct control of the microcomputer. When the external battery charging source is connected to the unit the pump is automatically forced on and into the OFF state. The microcomputer is able to sense the presence of the external charger voltage via external circuitry connected between the charging jack and the microprocessor. Charging is at the 10 hour rate of the battery, and over charge of the battery is precluded by timers in the microcomputer. At the end of a 14 hour charge cycle the microcomputer reverts to a trickle charge mode. The microcomputer has the ability to charge two different battery pack configurations. An input to the microcomputer indicates what type of battery pack, either a sub-C or ½ D pack, is connected to the unit.

Charging of the battery packs is done using a constant current DC-to-DC converter which is duty cycle controlled by the microcomputer to establish the proper charging currents for the two types of battery packs. The DC-to-DC converter is a self-oscillating design configured around an operational amplifier, typically a CA3130. The output of this operational amplifier gates on a transistor at the required repetition rate necessary to ensure continuous current flow in an inductor. The pulse rate is variable in the range of 100 to 150 Hz. In normal operation, the current level is established by adjusting a potentiometer which establishes the reference voltage to the inverting input of the operational amplifier. A diode performs the fly-back function to allow current to flow continuously through the inductor during the off time of the pulses. Two other diodes prevent discharge of the battery pack when the charger is not connected, and a zener diode clamps the voltage across the battery terminals to allow operation from the charger without the battery connected.

During charging the microcomputer gates the charging circuit on by controlling external transistor. When charging at the 10 hour rate, the sub-C and the ½ D batteries are gated at duty cycles of 40% and 80%, respectively. Under trickle charge the duty cycles drop to 10% and 20%, respectively. Battery charging is only performed when the microcomputer is in the OFF state and the full charge time of 14 hours is reinitiated any time the microcomputer is returned to that state after the motor has been turned on. While connected to the charger, all power to the unit is provided by the charger power supply and no energy is taken from the battery. When the motor is operating, the charge circuit is gated on in synchronism with the motor drive signal. Since the charger current is always greater than the motor current, no current can flow out of the battery. Discrete external circuitry ensures that the microcomputer and logic functions are also powered from the battery charger.

RECHARGEABLE BATTERY PACKS

As stated above the pump can be powered from either a sub-C or ½ D battery pack. Both packs contain 5 series connected nickel-cadmium cells and a 1.5 ohm current limiting resistor as well as a PTC (positive temperature coefficient) device. These are included in the battery pack to ensure compliance with the intrinsic safety requirements. Three terminals are required to the battery, two for the battery potential and the other as an indicator of the battery pack type. This third pin is connected to the negative terminal of the battery in the case of the ½ D battery and open in the sub-C battery pack.

PUMP FLOW CONTROLS

The pump air flow rate is controlled by the microcomputer using a pulse width modulation technique. The flow rate is sensed as function of the state of the pressure switch. To prevent arcing of the contacts of the pressure switch, voltage is only applied to the switch for 10 microseconds at a sample rate of 500 samples per second. This technique takes advantage of the inherent design of the 8049 bidirectional output pin circuit. During the time when a sample is not being taken, the output pin is held at ground potential and is only enabled as necessary to sample the state of the switch. During the on time of the sample pulse the current is limited to approximately 2 milliamps for less than 2 microseconds and then reverts to 50 microamp current level for the remainder of the 10 microsecond sample interval.

The control algorithm is a digital implementation of perfect integration second order control loop with the added sophistication of variable closed loop gain for maximum acquisition of the required pulse width to sustain the desired flow rate. In essence the closed loop system averages the on and off time of the pressure switch and forces the average to be 50%. After acquisition, the loop gain is reduced to minimum to prevent "hunting" when under closed loop control. For fast acquisition either caused by pump load changes or at power-up, the pump reverts to maximum loop gain which effectively increases the rate at which the duty cycle to the motor can change. As the motor speed comes closer to control, the gain is dropped to intermediate levels until absolute control is established. A low flow condition is declared when the duty cycle is forced to 97% and loop control is still not detected.

The pump can be programmed to shut down after a certain period of low flow operation. This period is programmable from 1 second–99 minutes and typically is 2 minutes.

One of the features available in an intelligent digital loop is the ability to remember the motor state after a run interruption. If at the time of turn-off the motor was under control, the duty cycle of the desired flow rate is remembered and this duty cycle is used when the pump is turned on again. This allows the pump to be restarted with a minimum turn on transient. If after a reapplication of power to the motor loop stabilization is not attained within a short period of time, the microcomputer reverts to the acquisition sequence.

The duty cycle to the pump motor is variable in steps of 0.1% from 3 to 97%. Since the pulse repetition rate is 20 Hz, this means that the minimum step size is 50 microseconds. The constraints on the control algorithm, in addition to this granularity and repetition rate, were that a real time base must be kept accurately and that the pressure switch must be sampled every 2 milliseconds. These requirements were also dovetailed into the limitations of the 8049 time interrupt subsystem.

We claim:
1. An improved pump unit for sampling air and having a constant air flow rate through the unit, the unit having an air intake, a filter means for removing particles or vapors from the air tubularly connected to the air intake, a variable drive air pump connected to the filter means which pump units an air stream through the unit, a variable speed electric motor connected to the pump and drives the pump, a power source for the motor, an orifice positioned in a tubular connection coupled to the pump and causes an air pressure drop in the air stream being pumped through the pump unit, a differential pressure switch with an open and a closed position tubularly placed in parallel relationship to the orifice and is activated by a change in air pressure drop of the air stream caused by a change in air flow through the unit, an exhaust port tubularly connected to the orifice and the differential pressure switch; the improvement used therewith comprises:

digital circuit electrically connected to the pressure switch and a closed loop control means electrically connected to the digital circuit, the power source and the motor; wherein the digital circuit sends a digital low duty cycle pulse signal over a set time interval to determine the predominant open or closed position of the switch during the time interval; in the event the switch is in the predominantly open position, the control means gradually increases voltage from the power source to the motor thereby driving the motor at an increasing speed which in turn drives the pump at an increasing speed and increases air flow through the unit; in the event the switch is in the predominantly closed position, the control means gradually decreases voltage from the power source to the motor thereby driving the motor at a decreasing speed which in turn drives the pump at a decreasing speed and decreases air flow through the unit; whereby the air flow through the unit is maintained at a constant flow rate.

2. The pump unit of claim 1 in which the closed loop control means comprises and integrator circuit electrically connected to the power source and the digital circuit and uses the signal from the digital circuit and integrates this signal; and an amplifier circuit electrically connected to the power source and connected in series to the integrator circuit and to the electric motor which amplifies the signal generated by the integrator circuit and feeds the amplified signal to the electric motor.

3. The pump unit of claim 1 in which the digital circuit provides pulses in the range of 50–1000 pulses per second to the pressure switch and the pulses have a duty cycle of 0.1–5% and effective current to the switch is limited to 0.1 to 5.0 milliamps.

4. The pump unit of claim 1 in which the closed loop control means comprises a digital integrator circuit connected to the digital circuit, a digital to analog converter connected to the integrator an amplifier circuit connected to the converter and to the motor; wherein the digital integrator receives a signal from the digital circuit on the pressure switch position and the signal is integrated and fed to the digital to analog converter which converts the signal and feeds the converted signal to the amplifier circuit and the signal is amplified and drives the motor and in turn the air pump at a desired speed to maintain uniform air flow through the unit.

5. The pump unit of claim 1 having an air accumulator positioned between the air intake and the pump.

6. The pump unit of claim 1 in which an air reservoir is tubularly connected between the pump and the orifice.

7. The pump unit of claim 1 having a filter positioned in a parallel tube before the pressure switch.

8. The pump unit of claim 1 in which the closed loop control means comprises a digital integrator circuit connected to the digital circuit, a digital pulse width modulator switching device connected to the integrator circuit the motor and power source, wherein the digital integrator receives a signal from the digital circuit on pressure switch position and the signal is integrated and fed to the switching device which feeds current to the motor and operated the motor and air pump to maintain a uniform air flow through the unit.

9. The pump unit of claim 8 in which a current limit circuit is electrically connected between the motor and the digital pulse modulator switching device and the motor; wherein the circuit limits maximum current pulses to the motor and increases pulse time for high current pulses.

10. The pump unit of claim 8 in which digital circuit and the closed loop control means are a part of computer circuit.

11. The pump unit of claim 10 having a temperature measuring circuit coupled to the computer.

12. The pump unit of claim 10 in which a driver unit is electrically coupled to the computer and is coupled to a liquid crystal display which shows data generated by the computer and has a key board coupled to the computer for entering operating parameters.

13. The pump unit of claim 12 having a device for attachment of a data buss for loading and unloading data.

14. The pump unit of claim 13 wherein a programmer unit can be attached to the device for the data buss for loading data.

15. The pump unit of claim 13 in which the bypass for the motor and the orifice each have an adjustable needle valve and the orifice is an adjustable needle valve.

16. The pump unit of claim 15 having a low air flow detector circuit.

17. The pump unit of claim 1 having an adjustable bypass connected in parallel with the pump and is used to adjust flow of air through the pump.

18. The pump unit of claim 17 in which the pump is a diaphragm pump.

19. The pump unit of claim 17 having a bypass tubularly connected in parallel to the orifice.

20. The pump unit of claim 1 in which the power source is a battery pack.

21. The pump unit of claim 20 having a battery charging circuit.

* * * * *